United States Patent [19]

Carden

[11] Patent Number: 4,633,890
[45] Date of Patent: Jan. 6, 1987

[54] ANAESTHETIST'S GAS POLLUTION INHIBITOR

[76] Inventor: Edward Carden, 53 Priestnall Rd., Stockport, United Kingdom

[21] Appl. No.: 677,995

[22] Filed: Dec. 4, 1984

[51] Int. Cl.⁴ .......................................... A61M 17/00
[52] U.S. Cl. ................... 128/910; 128/202.27
[58] Field of Search ............... 128/202.27, 910, 20.24; 433/77

[56] References Cited

U.S. PATENT DOCUMENTS

| | | | |
|---|---|---|---|
| 3,537,447 | 11/1970 | Garthier | 128/910 X |
| 4,248,218 | 2/1981 | Fischer | 128/910 X |
| 4,291,689 | 9/1981 | Hay | 128/910 X |
| 4,312,339 | 1/1982 | Thompson | 128/910 X |
| 4,506,665 | 3/1985 | Andrews et al. | 128/202.27 |
| 4,527,558 | 7/1985 | Hoenig | 128/910 X |

FOREIGN PATENT DOCUMENTS

| | | | |
|---|---|---|---|
| 2137788 | 12/1972 | France | 128/202.27 |
| 2070940 | 9/1981 | United Kingdom | 128/910 |

*Primary Examiner*—Edward M. Coven
*Attorney, Agent, or Firm*—James M. Skorich

[57] ABSTRACT

An apparatus for preventing the egress of anaesthetic gas from the open end of an anaesthesia tube during periods when the anaesthetic gas is flowing but it is not being administered to a patient. An obturator post is either solid or has an axial bore which communicates with an exhaust system. The obturator post slideably and sealably engages the open end of the anaesthesia tube. The obturator post may be either rigidly attached to a surface of the anaesthetist's machine, or held captive thereto by a chain.

17 Claims, 5 Drawing Figures

ANAESTHETIST'S GAS POLLUTION INHIBITOR

This invention concerns an anaesthetist's gas pollution inhibitor, in an anaesthesia machine.

In the practicing of surgery and anaesthesiology, more and more consideration has been given, in recent years, to the operating theatre atmosphere and the problems of air-borne transmission of infection, as well as the presence in the atmosphere of pollutants, such as anaesthetic gas, which may have an adverse effect upon the surgeon and/or his supporting operating theatre staff.

Anaesthesia machines are usually fitted with exhaust systems intended to conduct any leaking gas to a specific location on the machine, from which it can then be drawn away, e.g. into a discharge system, to be discharged at a safe location away from the operating theatre. Such arrangements are effective for anaesthesia machines in general. However, they do have the disadvantages that they do not make any provision for collecting and conducting away any gases which may leak from the usual flexible anaesthesia tubing which, in the use of the machine, will normally be connected to a face mask or an endotracheal tube applied to or for application to a patient. When the anaesthesia tube and face mask are taken away from the patient's face, or when the anaesthesia tube is uncoupled from the face mask or endotracheal tube as aforesaid, there may be gas leakage, to the detriment of nearby operating theatre staff and as will be understood, the presently-provided instrumentalities on anaesthetic machines do not provide any safeguard against this.

An object of the present invention is to provide a very simple, inexpensive and convenient arrangement whereby gas leakage from an anaesthesia tube aforesaid may be inhibited or obviated, and which has the added advantage that it provides for the said anaesthesia tube to be located in a constant and readily-determinable position whenever it is not required for use, and wherefrom it can be retrieved rapidly, when it is next required for use.

With this object in view, the present invention provides an anaesthesia machine including a flexible anaesthesia tube having a free end adapted for plug-in or plug-on coupling therewith of a face mask or endotracheal tube, characterised in that the machine further includes an obturator post adapted for the free end of the anaesthesia tube to fit thereon, thereby to plug said free end against gas leakage.

The obturator post may, if desired, simply be held captive to the machine by being connected thereto by a chain. Preferably, however, the post has, on one end, a base part or flange by which it is secured (e.g. by adhesion) to a suitable surface of the machine.

The post may be of any suitable material such as aluminum or stainless steel, and may be generally of tubular configuration including a constant-diameter base section and a tapered end section for the anaesthesia tube to be a friction fit thereon.

The invention will be described further, by way of example, with reference to the accompanying drawing, in which.

It is to be understood that the following details are illustrative, and not restrictive, of the scope of the invention.

Figure 1:
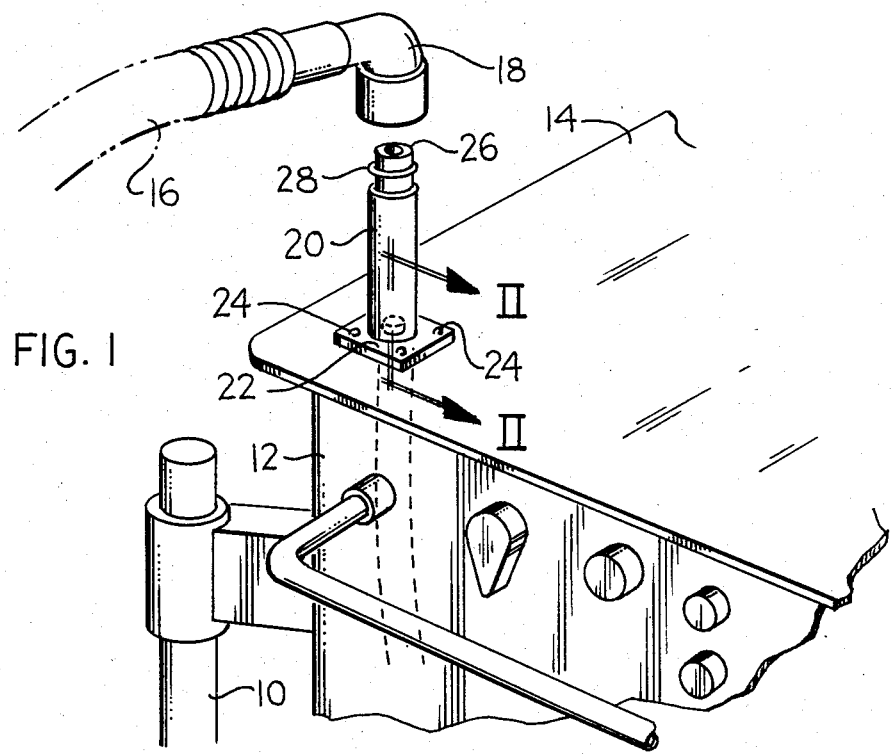
FIG. 1 is a fragmentary perspective view illustrating a practical embodiment of the pollution inhibitor of the invention.
Figure 2:
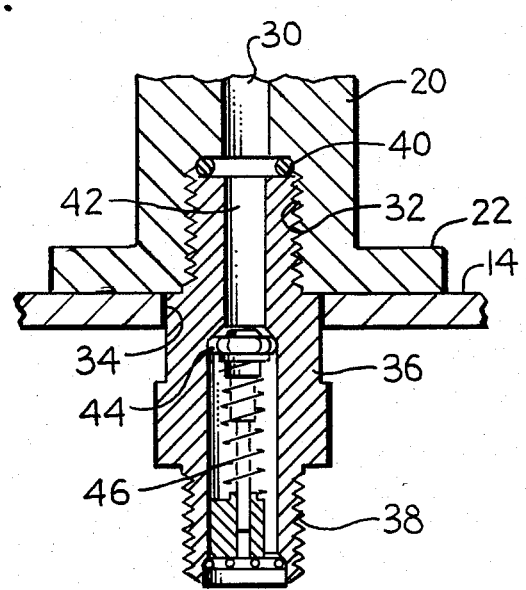
FIG. 2 is an enlarged fragmentary sectional view illustrating the lower part of the pollution inhibitor of FIG. 1; the section corresponding to the line II—II of FIG. 1.

Referring firstly to FIGS. 1 and 2, a first preferred embodiment of the anaesthesia machine according to the invention is in general of conventional configuration in the form of a trolley-like structure part of which is shown in FIG. 1, and having upright corner columns 10 with free-running castors (not shown) at their lower ends and supporting a flat-topped body or housing 12 enclosing control equipment (not illustrated in detail) for anaesthetist's gas cylinders for which there are appropriate carriers or racks (not specifically shown). Top 14 of the body or housing 12 may, of course, provide a support surface for a wide range of equipment, accessories, materials and/or reagents (not shown) useful to an anaesthetist using the machine, as may be desired.

The control equipment provides an anaesthetic gas outlet spigot (not shown) onto which fits an anaesthesia tube 16 which is of fairly large diameter, for instance of the order of 2 to 3 cms, and has at one end (not shown) a taper socket for fitting, as a friction fit, onto the spigot. At its other or free end, which is illustrative in FIG. 1 and anaesthesia tube 16 is formed with a right-angled socket-end 18 having a tapered inside diameter for being a friction fit onto a tapered connector (not shown) to a face mask or to an endotracheal tube, neither of which is shown, but both of which are coventional anaesthetic accessories.

Secured to the top 14 of the body or housing 12 is an obturator post 20. This post, in the illustrated case, is a hollow or tubular sleeve-like element of constant cross-section over the majority of its height and formed integrally at its bottom end with a rectangular flange 22. This post 20 is made, for instance, of polished aluminium or stainless steel, and it is fixed, in the illustrated case, to the top 14 of the body or housing 12 by suitable screws 24 through the flange 22. As an alternative, the flange could be secured in place by means of an appropriate resinous adhesive, e.g. an epoxy resin or a methacrylate.

At its upper end, the post 20 has a reduced diameter top portion 26 about midway up the height of which is a circumferential groove (not visible) in which a sealing ring 28, which is an O-ring, is accommodated.

The purpose of the obturator post 20 will readily be understood from the foregoing description. It is to provide a location onto which the free socket end 18 of the anaesthesia tube 16 can be pushed or fitted when it is not connected to a face mask or endotracheal tube. Then, if there should be a leakage of gas past the controls and into the anaesthesia tube 16, this gas will be prevented from emerging from the anaesthesia tube by reason of it being plugged by the obturator post 20. The O-ring 28 ensures sealing between the post 20 and the socket end 18 and if, as may be the case, the post 20 is solid, the post 20 serves as a stopper plug for the tube 16, and prevents emergence of anaesthetic gas as aforesaid.

So long as the post 20 is of sufficient length, it may be possible to push the socket end 18 of the tube 16 onto the post 20 whilst a face mask is still in position on said socket end 18.

Figure 4:
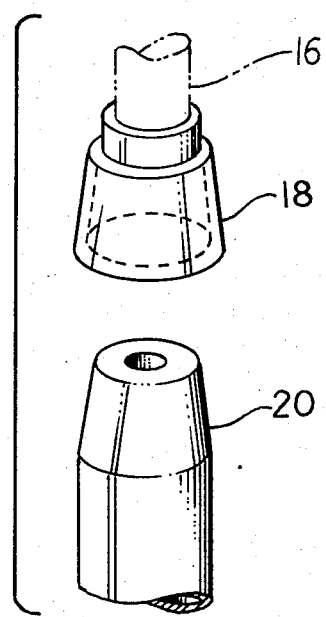
FIG. 4 is an enlarged fragmentary perspective view illustrating the upper part of a third embodiment of the pollution inhibitor of the invention.

Instead of being of reduced diameter at its upper end at 26 as shown in FIG. 1, the post 20 may be provided with a standard frusto-conical top end or taper for providing a sealing fit with a corresponding internal taper in the socket end 18. This embodiment is illustrated in FIG. 4.

Where the post 20 is solid as above mentioned, it does not have to be stationarily fixed to the anaesthesia machine; it may, if desired, simply be anchored to the latter by some suitable relatively-permanent connecting means, such as a chain or stainless steel cable.

The illustrated post 20 is not solid as above proposed. Instead, as can be seen in detail in FIG. 2, the post 20 has therethrough an axial bore 30. At its lower end, this bore 30 is formed with a threaded entry 32 which registers with an opening 34 through the top 14 of the housing 12 to receive a non-return valve 36 adapted, at its lower end 38, for connection to an exhaust system (not shown). As shown, this valve 36 is sealed relative to the bore 30 by its inner end abutting a sealing ring 40 and has a through-passage 42 possessing a step or shoulder against which a sealing washer 44 is lightly loaded by a spring 46 to prevent any possibility of reverse passage of gas through the post 20 into the tube 16.

Accordingly, in this specific embodiment, any anaesthetic gas which may leak to the end-piece 18, instead of just being plugged off by the post 20, is able to pass through the bore 30 in the post 20, and thence through the non-return valve 36 to the exhaust system.

Figure 5:
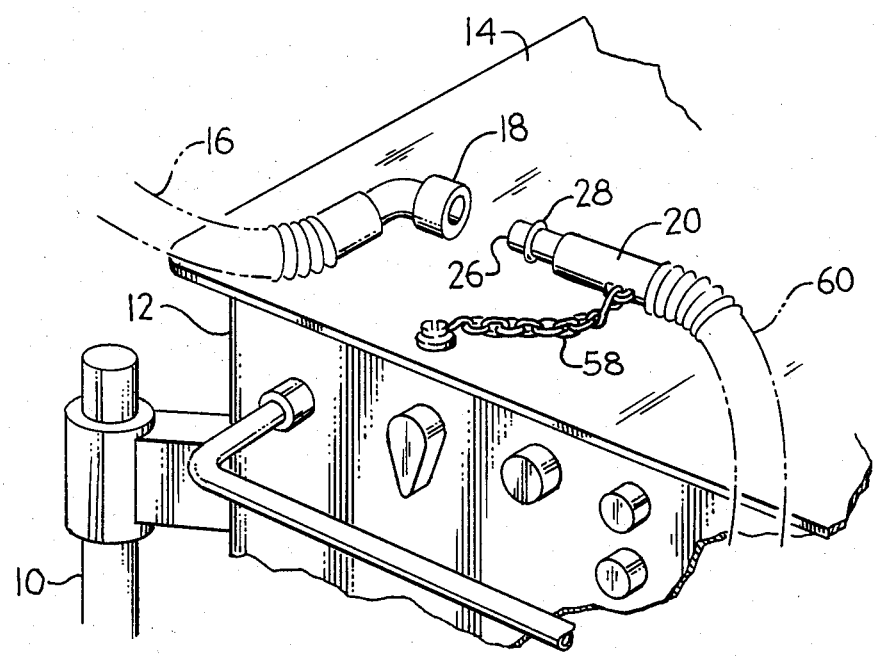
FIG. 5 is a fragmentary perspective view illustrating another embodiment of the invention wherein the pollution inhibitor is tethered to the anaesthesia machine by a chain.

FIG. 5 illustrates another embodiment of the invention wherein post 20 is tethered to top 14 of housing 12 by chain 58. As is the case for the embodiment drawn in FIG. 1, axial bore 30 (not shown) passes longitudinally through post 20. Axial bore 30 communicates with an exhaust system (not shown) through exhaust hose 60.

The obturator post 20 accordingly provides, in a very simple and convenient manner, a very effective way of ensuring that any gas unintentionally reaching the anaesthesia tube 16 is prevented from emerging into the atmosphere in which the anaesthetic apparatus is disposed (e.g. the operating theatre); moreover, it assures that the anaesthesia tube 16, when not in use, is put away in a predetermined location from which it can be retrieved easily and with confidence.

Figure 3:
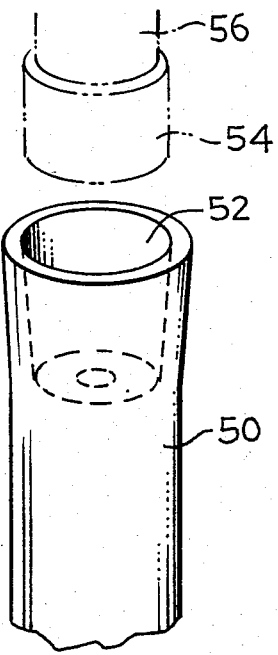
FIG. 3 is an enlarged fragmentary perspective view illustrating the upper part of a second embodiment of the pollution inhibitor of the invention.

The invention is not confined to the precise details of the foregoing example, and variations may be made thereto. Thus, as has already been mentioned, the obturator tube 20 may be of any convenient form or configuration for the free end of the anaesthesia tube 16 to fit thereto, and it does not have to be stationarily fixed or mounted on the anaesthetist's machine, but may be movably anchored thereto, e.g. by a chain or the like. As shown in FIG. 3 the arrangement may be such that the post, here indicated by the reference numeral 50, is provided at its upper end with an internal socket 52 for the appropriate end 54 of the anaesthetic tube 56 to fit therein. As shown, this may be a taper fit, but of course it could be a parallel fit with a sealing ring as in the arrangement of FIG. 1.

What is claimed is:

1. Apparatus for preventing the undesirable egress of anaesthetic gas into ambient atmosphere comprising:

a tube having one end connected to an anaesthesia machine and its second end being a free end;

said anaesthesia machine supplying anaesthetic gas to said tube;

said free end being removably connectable to a breathing passage of a patient;

an obturator post connected to said anaesthesia machine and constructed to sealingly engage said free end, for preventing the undesirable egress of said anaesthetic gas into the atmosphere of an operating theater when said free end is disconnected from said breathing passage; and a bore passing through said obturator post and communicating with exhaust means.

2. The invention as defined in claim 1 further comprising:

means located on said post for sealing said engagement between said obturator post and said free end.

3. The invention as defined in claim 2 wherein:

said obturator post and said tube are cylindrical;

said post engages the inside diameter of said obturator tube; and said sealing means is comprised of a flexible ring situated circumferentially about said obturator post.

4. The invention as defined in claim 3 wherein:

said bore contains a pressure sensitive valve which allows gas to flow only from said free end into said exhaust means.

5. The invention as defined in claim 4 wherein:

said obturator post is rigidly attached at one of its ends to a suitable surface of said anaesthesia machine.

6. The invention as defined in claim 4 wherein:

said obturator post is held captive to said anaesthesia machine by means of a tether.

7. The invention as defined in claim 1 wherein:

said bore includes a pressure sensitive valve which allows gas to flow only from said free end into said exhaust means.

8. The invention as defined in claim 7 wherein:

said obturator post is rigidly attached at one of its ends to a suitable surface of said anaesthesia machine.

9. The invention as defined in claim 7 wherein:

said obturator post is held captive to said anaesthesia machine by means of a tether.

10. The invention as defined in claim 1 wherein:

the end of said obturator post constructed to sealingly engage said free end has a frusto-conical shape.

11. The invention as defined in claim 10 wherein:

said bore includes a pressure sensitive valve which allows gas to flow only from said free end into said exhaust means.

12. The invention as defined in claim 11 wherein:

said obturator post is rigidly attached at one of its ends to a suitable surface of said anaesthesia machine.

13. The invention as defined in claim 11 wherein:

said obturator post is held captive to said anaesthesia machine by means of a tether.

14. The invention as defined in claim 1 wherein:

said tube being cylindrical;

said obturator post having a female end which engages said free end of said tube, and a base end; and said female end being concave and shaped to engage the outside diameter of said free end of said tube.

15. The invention defined in claim 14 wherein:

said bore contains a pressure sensitive valve which allows gas to flow only from said free end into said exhaust means.

16. The invention as defined in claim 15 wherein: said obturator post is rigidly secured at one of its ends to a suitable surface of said anaesthesia machine.

17. The invention as defined in claim 15 wherein: said obturator post is held captive to said anaesthesia machine by means of a tether.

* * * * *